United States Patent [19]
Nita

[11] Patent Number: 6,007,514
[45] Date of Patent: Dec. 28, 1999

[54] ULTRASOUND SYSTEM WITH PATHFINDING GUIDEWIRE

[76] Inventor: Henry Nita, 1775 Milmont Dr., Unit D. #306, Milpitas, Calif. 95035

[21] Appl. No.: 08/940,629

[22] Filed: Sep. 30, 1997

[51] Int. Cl.[6] .............................. A61B 17/20; A61B 17/32
[52] U.S. Cl. ............................................. 604/22; 606/169
[58] Field of Search ............................ 604/22, 113, 508, 604/510, 523; 600/434, 439; 601/2; 606/107, 169

[56] References Cited

U.S. PATENT DOCUMENTS

| | | | |
|---|---|---|---|
| 3,631,848 | 1/1972 | Muller | 128/348 |
| 4,811,743 | 3/1989 | Stevens | 128/772 |
| 4,870,953 | 10/1989 | DonMichael et al. | 128/24 A |
| 5,267,954 | 12/1993 | Nita | 604/22 |
| 5,269,291 | 12/1993 | Carter | 128/24 AA |
| 5,304,115 | 4/1994 | Pflueger et al. | |
| 5,312,328 | 5/1994 | Nita et al. | 604/22 |
| 5,324,255 | 6/1994 | Passafaro et al. | 604/22 |
| 5,342,292 | 8/1994 | Nita et al. | 604/22 |
| 5,368,558 | 11/1994 | Nita | 604/22 |
| 5,380,274 | 1/1995 | Nita | 604/22 |
| 5,382,228 | 1/1995 | Nita et al. | 604/22 |
| 5,427,118 | 6/1995 | Nita et al. | |
| 5,611,807 | 3/1997 | O'Boyle | 606/169 |
| 5,618,266 | 4/1997 | Liprie | 604/21 |

*Primary Examiner*—Ronald K. Stright, Jr.
*Assistant Examiner*—Patricia M. Bianco
*Attorney, Agent, or Firm*—Raymond Sun

[57] ABSTRACT

A system is provided that allows completely occluded blood vessels to be crossed. The system includes a pathfinding guidewire that is coupled to the distal end of an ultrasound catheter. The distal section of the pathfinding guidewire acts as a narrow extension of the distal end of the catheter which is effective in transmitting ultrasound energy to cross occlusions. Once the distal section of the guidewire has crossed the occlusion, the distal end of the catheter can be advanced over the distal section of the guidewire and against the occlusion to remove the occlusion.

13 Claims, 6 Drawing Sheets

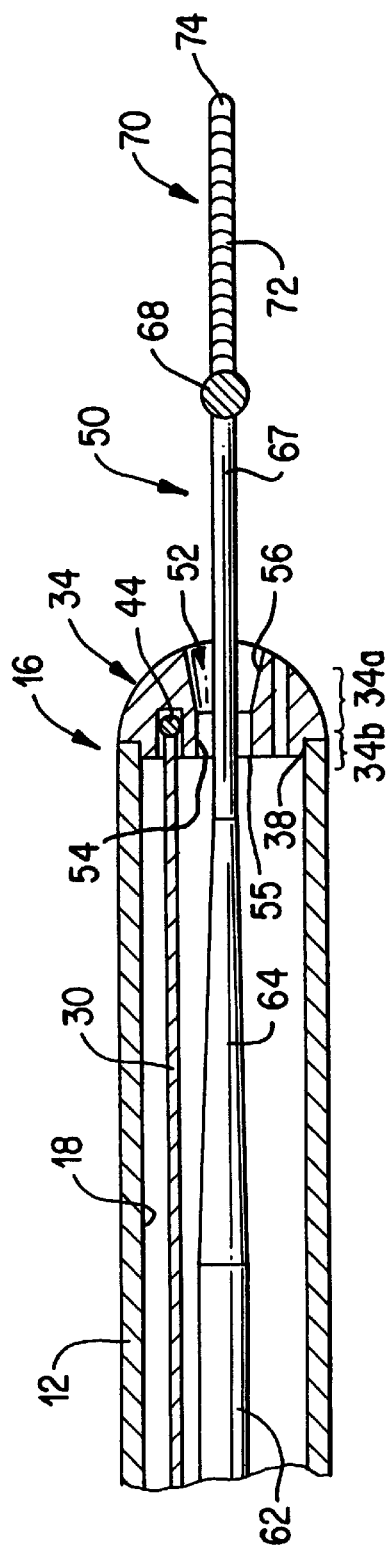
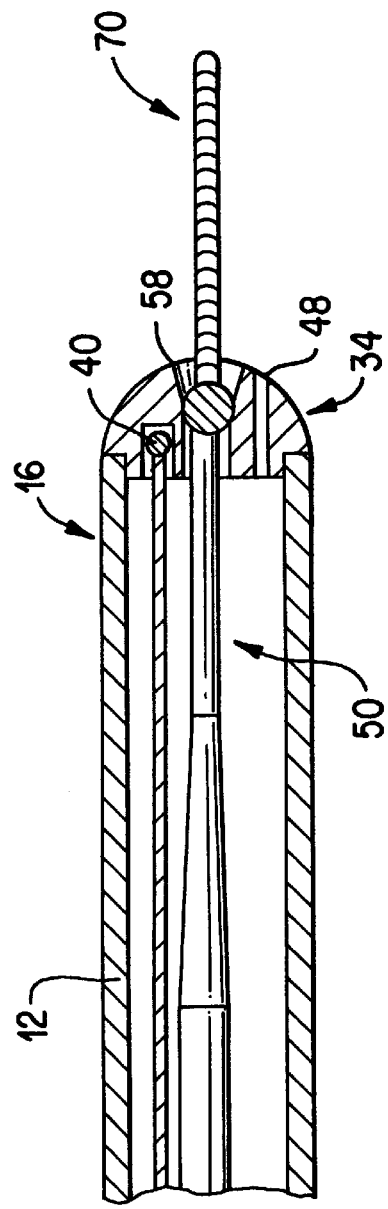
FIG. 2
FIG. 3

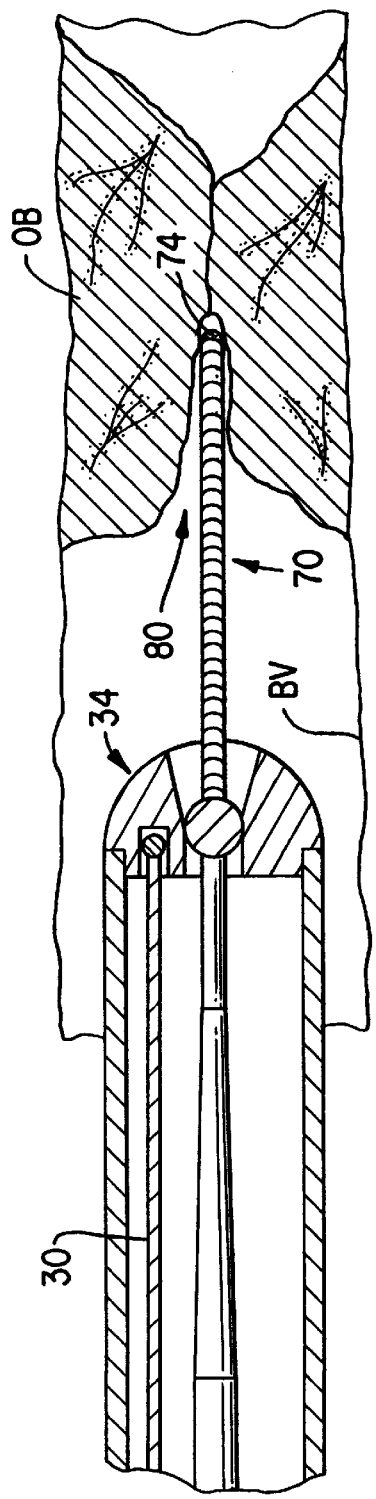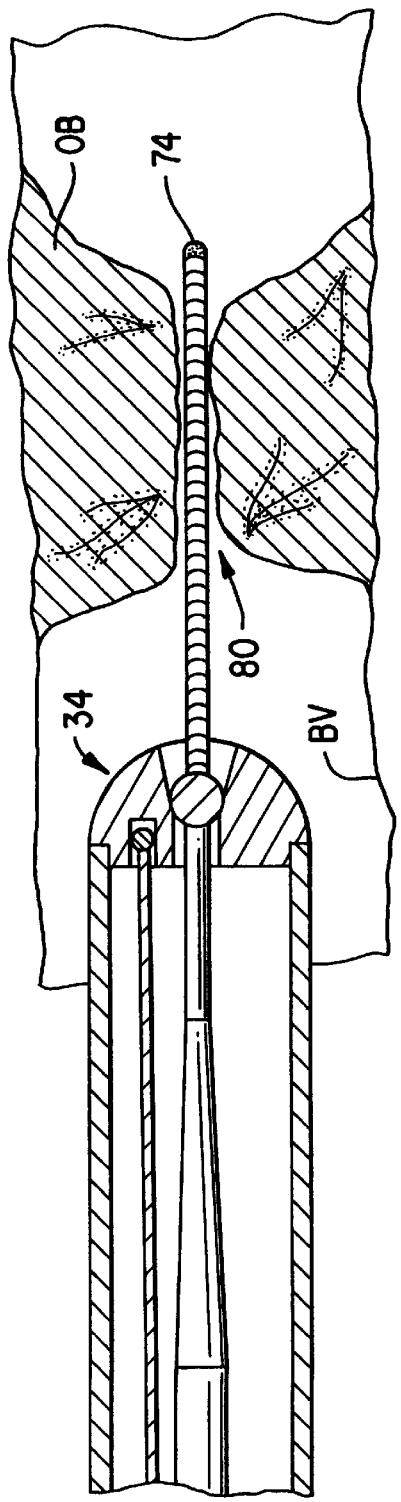

ULTRASOUND SYSTEM WITH PATHFINDING GUIDEWIRE

BACKGROUND OF THE INVENTION

1. Field of the Invention

The present invention pertains to an ultrasound catheter system for ablating obstructions within tubular anatomical structures such as blood vessels, and in particular, an ultrasound catheter system that is capable of crossing completely occluded obstructions in a blood vessel.

2. Description of the Prior Art

A number of ultrasound catheter systems have heretofore been proposed for use in ablating or removing obstructive material from blood vessels. These ultrasound catheter systems include an ultrasound transmission member incorporated with a catheter for transmitting ultrasound energy to the obstructive material to remove the obstructive material. The catheter is delivered percutaneously to the location of the obstruction with the aid of a guidewire. Specifically, the guidewire is first percutaneously advanced through the patient's vasculature until it reaches and crosses the region of the blood vessel where the obstructive material is located. The catheter carrying the ultrasound transmission member is then advanced along the guidewire to the location of the obstructive material. The distal tip of the catheter is caused to contact the obstructive material, and ultrasound energy is then applied to the distal tip of the catheter via the ultrasound transmission member, to remove the obstructive material. The catheter is advanced along the guidewire through the obstructive material until the distal tip of the catheter has passed through all the obstructive material. In some instances, adjunctive balloon angioplasty (PTCA) can be performed to achieve better results.

Thus, the ultrasound systems and devices described above have been effective in removing obstructive material in blood vessels when it has been possible to cross the obstructed region with a guidewire. Since the guidewire is needed to guide the distal tip of an ultrasound catheter through the obstructed region, these ultrasound catheter systems are ineffective in treating a blood vessel which has been completely occluded by obstructive material, where the guidewire is not able to cross the obstructive material at the obstructed region.

Completely occluded obstructions are also troublesome since the number of treatment options are limited. For example, PTCA or balloon angioplasty procedures cannot be carried out to ablate completely occluded obstructions because it is not possible to place an expandable balloon inside the obstructed region. In addition, ultrasound catheter systems, such as those described above, are ineffective for the reasons explained above. Of the remaining options, highly invasive alternatives such as cardiovascular surgery are possible, but are undesirable.

There are also available less invasive techniques such as laser techniques and cutting techniques such as atherectomy and thrombectomy where rotational cutters, shavers, and coring means are used to cut through the occlusion. However, not only do these less invasive techniques also require that a guidewire be used to cross the obstructed region, but they also have additional drawbacks. For example, the cutting techniques require the use of cutting devices that are often bulky in nature, and therefore cannot be used, without a guidewire, to cut obstructive material. In addition, there is always a possibility that some of these cutting devices may damage or even perforate the blood vessel wall if they are not used with guidewire support.

Further, the laser techniques, when used without guidewire support, may perforate the vessel wall, and can cause mechanical thermal damage or necrosis, which kills healthy cells and nerves. Laser systems for providing the laser energy can also be expensive.

One attempt to address this problem is illustrated in U.S. Pat. No. 5,427,118 to Nita et al., in which an ultrasonic guidewire is provided for crossing completely occluded blood vessels. The ultrasonic guidewire creates the necessary pathway through the obstructive material, and a balloon catheter is then advanced inside the obstructive material and the balloon expanded to dilate the obstructive material. Unfortunately, the ultrasonic guidewire in U.S. Pat. No. 5,427,118 is not by itself fully effective in removing the obstructive material because the low profile throughout the length of the guidewire means that an insufficient amount of ultrasound energy is transmitted from the transducer to the distal end for treating the occlusion.

Thus, there still exists a need for improved ultrasound systems having ultrasound catheters that can treat and remove obstructive material from fully occluded blood vessels.

SUMMARY OF THE DISCLOSURE

In order to accomplish the objects of the present invention, there is provided an ultrasound system having a catheter with a flexible catheter body, and an ultrasound transmission member extending longitudinally through the lumen of the catheter body, the ultrasound transmission member having a proximal end connectable to a separate ultrasound generating device. The catheter also includes a distal head positioned on the distal end of the ultrasound transmission member. A guidewire is coupled to and extends distally of the distal head.

The guidewire according to the present invention has a constant-diameter proximal section, and a tapered section extending distally from the proximal section and having a distal end. The guidewire further includes an enlarged member provided at the distal end of the tapered section, and a distal section extending distally from the enlarged member. The enlarged member has a diameter that is greater than the dimension of the distal end of the tapered section.

In one embodiment of the present invention, the distal head has a bore extending longitudinally therethrough, with the guidewire removably engaged inside the bore. The bore has a flared distal section with a distal opening and a proximal opening, the distal opening having a larger diameter than the proximal opening of the distal section. The enlarged member of the guidewire is removably engaged to the distal section of the bore. Ultrasound energy is applied via the ultrasound transmission member, the distal head and the enlarged member to the distal section of the guidewire when the guidewire is engaged with the distal head.

In another embodiment of the present invention, the bore has a flared proximal section with a distal opening and a proximal opening that opens to the lumen of the catheter body, the proximal opening having a larger diameter than the distal opening of the proximal section. The enlarged member of the guidewire is removably engaged to the proximal section of the bore. Ultrasound energy is applied via the ultrasound transmission member, the distal head and the enlarged member to the distal section of the guidewire when the guidewire is engaged with the distal head.

In yet another embodiment of the present invention, the guidewire is permanently attached to the distal head.

In one embodiment of the present invention, the ultrasound transmission member has a proximal region adjacent the proximal end, an enlarged distal end, and an intermediate region between the proximal region and the distal end. The intermediate region has a dimension which is smaller than the dimension of the proximal region. The enlarged distal end of the ultrasound transmission member has a dimension which is larger than the dimension of the distal end of the intermediate region.

In another embodiment of the present invention, the ultrasound transmission member has a proximal section and a spherical distal tip having a diameter which is preferably larger than the outer diameter of the transmission member along the proximal section.

The present invention also provides a method of crossing an occlusion inside a blood vessel. The method first provides a system having an elongate flexible catheter body, an ultrasound transmission member extending longitudinally through the lumen of the catheter body, and a distal head positioned on the distal end of the ultrasound transmission member. The method then delivers a guidewire inside the blood vessel to the site of the occlusion, and couples the guidewire to the distal head. Ultrasound energy is delivered to the guidewire via the distal head to creates a channel in the occlusion to thereby cross the occlusion.

Thus, the ultrasound systems according to the present invention provide a pathfinding guidewire that is coupled to the distal end of an ultrasound catheter. The distal section of the pathfinding guidewire acts as a narrow extension of the distal end of the catheter which is effective in transmitting ultrasound energy to cross occlusions. Once the distal section of the guidewire has crossed the occlusion, the distal end of the catheter can be advanced over the distal section of the guidewire and against the occlusion to remove the occlusion.

BRIEF DESCRIPTION OF THE DRAWINGS

FIG. 2 is a cross-sectional view of the distal end of a first embodiment of an ultrasound catheter and guidewire that can be used with the system of FIG. 1;

FIG. 3 is a cross-sectional view of the distal end of the ultrasound catheter of FIG. 2 shown with the guidewire secured at the distal tip of the catheter;

FIGS. 8A–8C illustrate how the ultrasound catheter and guidewire of FIG. 2 can be used to cross a completely obstructed blood vessel and to remove obstructive material therefrom.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
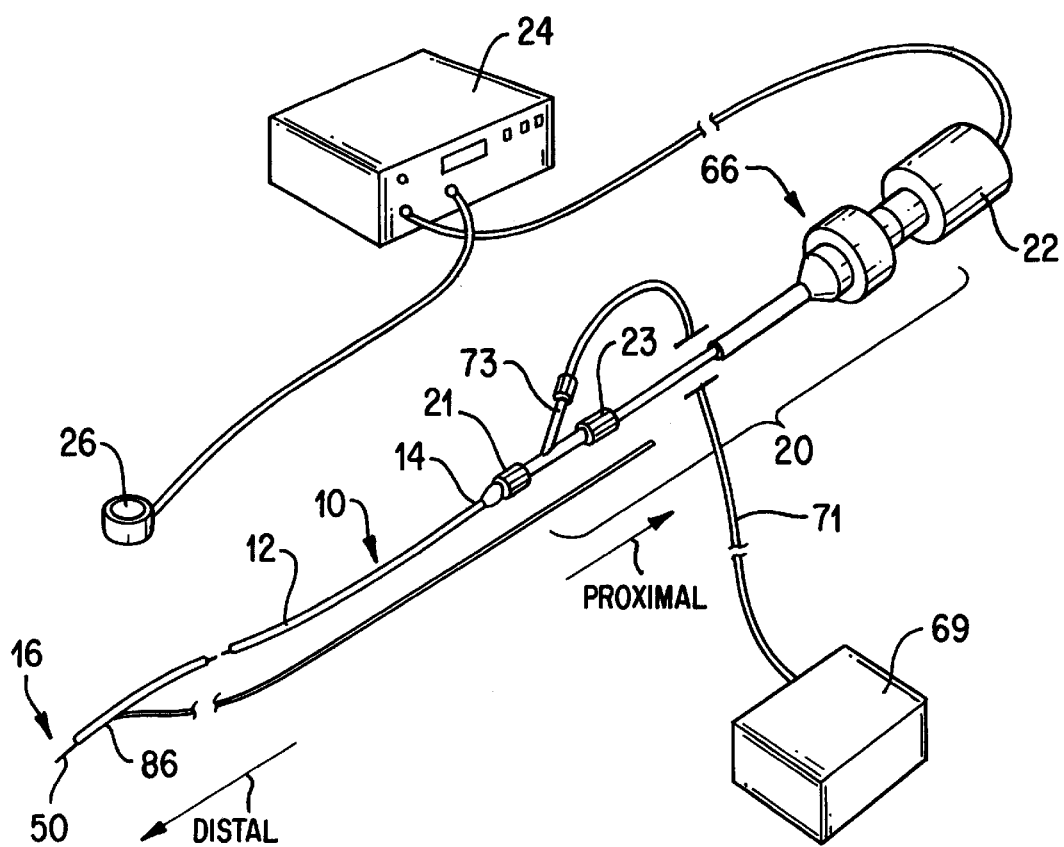
FIG. 1 is a perspective view of an ultrasound catheter and guidewire system according to the present invention.

FIG. 1 illustrates an ultrasound system according to the present invention for use in crossing a completely occluded region of a blood vessel and for removing the occlusive material. The ultrasound system includes an ultrasonic catheter device 10 which has a deflectable elongate catheter body 12 having a proximal end 14, a distal end 16, and defining at least one lumen extending longitudinally therethrough. The ultrasound catheter device 10 is operatively coupled, by way of a proximal connector assembly 20, to an ultrasound transducer 22. The ultrasound transducer 22 is connected to a signal generator 24. The signal generator 24 is provided with a foot actuated on-off switch 26. When the on-off switch 26 is depressed, the signal generator 24 sends an electrical signal to the ultrasound transducer 22, which converts the electrical signal to ultrasound energy. Such ultrasound energy subsequently passes through the catheter device 10 and is delivered to the distal end 16 of the catheter body 12. A guidewire 50 may be utilized in conjunction with the catheter device 10, as will be more fully described below.

One non-limiting embodiment of the distal end 16 of the catheter body 12 of the catheter device 10 is illustrated in FIGS. 2–3. In a preferred embodiment, the catheter body 12 is formed of a flexible polymeric material, for example, nylon (Pebax) manufactured by Atochimie, Cour be Voie, Hauts Ve-Sine, FRANCE. The flexible catheter body 12 is preferably in the form of an elongate tube having one or more lumens extending longitudinally therethrough.

Referring to FIG. 2, the catheter body 12 has one lumen 18. Extending longitudinally through the lumen 18 of the catheter body 12 is an elongate ultrasound transmission member 30 having a proximal end which is connectable to the ultrasound transducer 22 such that ultrasound energy will pass through the ultrasound transmission member 30. As such, when the foot actuated on-off switch 26 operatively connected to the ultrasound transducer 22 is depressed, ultrasound energy will pass through the ultrasound transmission member 30 to the distal end 16 of the catheter body 12. More particularly, the ultrasound transmission member 30 serves to transmit the ultrasound energy from the proximal connector assembly 20 to a distal head 34 mounted on the distal end 16 of the catheter body 12.

The distal head 34 has a substantially rigid member affixed to the distal end 16 of the catheter body 12. In the embodiment shown, the distal head 34 has a generally rounded distal portion 34a, and a generally cylindrical proximal portion 34b. The outer diameter of the proximal portion 34b is slightly less than the outer diameter of the distal portion 34a, defining an annular shoulder 38 to which the distal end 16 of the catheter body 12 is attached. Preferably, the outer diameter of the catheter body 12 is about the same as the outer diameter of the distal portion 34a, thereby forming a generally smooth outer surface at the juncture of the distal head 34 and the catheter body 12, as shown in FIG. 2.

The attachment of the distal head 34 and the catheter body 12 may be accomplished by any suitable manner. One manner is through the use of an adhesive which is applied to the interfacing surfaces to be attached. The adhesive may comprise any suitable adhesive, such as cyanoacrylate (e.g., Loctite Corp., Ontario, Canada or Aron Alpha, Borden, Inc., Columbus, Ohio) or polyurethane (e.g., Dymax, Dymax Engineering Adhesive, Torrington, Conn.). As an alternative to the use of adhesives, various mechanical or frictional connections, such as screw threads, lugs, or other surface modifications formed on one surface, can also be used, with corresponding grooves, detents, or surface modifications formed in the interfacing surface to be attached.

The distal head 34 may be formed of any suitable rigid material, such as metal or plastic. The distal head 34 is preferably formed of radiodense material so as to be easily discernible by radiographic means. Accordingly, the distal head 34 may preferably be formed of metal or, alternatively, may be formed of plastic, ceramic, glass, or rubber materials, optionally having one or more radiopaque markers affixed thereto or formed therein. For example, the distal head 34 may be molded of plastic, such as acrylonitrile-butadine-styrene (ABS) and one or more metallic marker-trips or other radiopaque markers may be affixed to such plastic distal head 34 in order to impart sufficient radiodensity to permit the distal head 34 to be readily located by radiographic means. Additionally, in embodiments wherein the distal head 34 is formed of molded plastic or other non-metallic material, a quantity of radiodense fillers, such as powdered Bismuth or Barium Sulfate ($BaSO_4$) may be disposed within the plastic or other non-metallic material of which the distal head 34 is formed so as to impart enhanced radiodensity thereto.

The ultrasound transmission member 30 extends through the lumen 18 and a bore 40 which extends longitudinally into the proximal portion 34b of the distal head 34. Referring to FIG. 2, the transmission member 30 has a spherical distal tip or ball 44 having a diameter which is preferably larger than the outer diameter of the transmission member 30 along its length. The ball 44 is received into, and is welded, bonded or attached to, the bore 40 of the distal head 34. The ball 44 provides a larger cross-sectional dimension at the distal-most part of the transmission member 30 to tolerate stress associated with the attachment of the ball 44 to the distal head 34. Alternatively, and instead of the ball 44, the distal end of the ultrasound transmission member 30 can be provided in the same diameter as the remainder of its length and can be firmly held within the bore 40 by the frictional engagement thereof to the surrounding material of the distal head 34, or by other mechanical or chemical affixation means such as but not limited to weldments, adhesive, soldering and crimping. Firm affixation of the ultrasound transmission member 30 to the distal head 34 serves to facilitate direct transmission of the quanta of ultrasonic energy passing through the ultrasound transmission member 30 to the distal head 34. As a result, the distal head 34, and the distal end 16 of the catheter device 10, are caused to undergo ultrasonic vibration in accordance with the combined quanta of ultrasonic energy being transmitted through the ultrasound transmission member 30.

In the preferred embodiment, the ultrasound transmission member 30 may be formed of any material capable of effectively transmitting the ultrasound energy from the ultrasound transducer 22 to the distal head 34, including but not necessarily limited to metal, plastic, hard rubber, ceramic, fiber optics, crystal, polymers, and/or composites thereof. Such materials should preferably exhibit good stress and strain characteristics. In accordance with one aspect of the invention, all or a portion of the ultrasound transmission member 30 may be formed of a nickel-titanium alloy. In particular, the nickel-titanium alloy preferably exhibits the following physical properties:

| PROPERTY | UNIT | VALUE |
| --- | --- | --- |
| Nickel | Atomic Weight | Min. 50.50 - Max. 51.50 |
|  | Weight Percent | Min. 55.50 - Max. 56.07 |
| Titanium | % | Remainder |
| Total gas content (O, H, N) | % | 0.15 Max |
| Carbon Content | % | 0.010 Max |
| Maxinium Tensile Strength | PSI | 220K |
| Elongation | % | 10–16 |
| Melting Point | Celcius | 1300–1350 |
| Density | $g/cm^3$ | 6.5 |

This alloy provides an ultrasound transmission member 30 that experiences minimum attenuation of ultrasound energy, and which has the ability to be navigated through the complex bends of tortuous vessels without experiencing any permanent deformation which would otherwise result in transmission losses.

Referring back to FIG. 1, the proximal connector assembly 20 of the catheter device 10 has an elongate, rigid body defining frontal, mid and rear portions. The frontal portion of the body is firmly connected to the proximal end 14 of the catheter body 12 via a threaded gripping member 21 engaged thereto. In this respect, the proximal end 14 of the catheter body 12 preferably has a flared configuration and includes an annular flange formed on the outermost end thereof which is brought into sealed engagement with the proximal connector assembly 20 when the gripping member 21 is threadably engaged to the body 12. The proximal end of the frontal portion is connected to the distal end of the mid-portion of the body via a second gripping member 23. To facilitate the aforementioned construction, threads are formed on the distal ends of the frontal and mid-portions of the proximal connector assembly 20. The extreme proximal end of the rear portion of the proximal connector assembly 20 is provided with a sonic connector assembly 66 which is configured to effect operative attachment of the proximal end of the ultrasound transmission member 30 to the horn of the ultrasound transducer 22. The sonic connector assembly or apparatus is preferably configured and constructed to permit passage of ultrasound energy through the ultrasound transmission member 30 with minimal lateral side-to-side movement of the ultrasound transmission member 30 while, at the same time, permitting unrestricted longitudinal forward/backward vibration or movement of the ultrasound transmission member 30.

In the ultrasound system according to the present invention, an injection pump 69 may be connected, by way of an infusion tube 71, to an infusion port or sidearm 73 in the frontal portion of the proximal connector assembly 20. The injection pump 69 is used to infuse coolant fluid (e.g., 0.9% NaCl solution) into and/or through the catheter device 10, and more particularly into the lumen 18 of the catheter body 12. Such flow of coolant fluid may be utilized to prevent overheating of the ultrasound transmission member 30 extending longitudinally through the lumen 18. Due to the desirability of infusing coolant fluid into the catheter body 12, at least one fluid outflow channel 48 extends longitudinally through the distal head 34 to permit the coolant fluid to flow from the lumen 18 out of the distal end 16 of the catheter body 12. Such flow of the coolant fluid through the lumen 18 serves to bathe the outer surface of the ultrasound transmission member 30, thereby providing for an equilibration of temperature between the coolant fluid and the ultrasound transmission member 30. Thus, the temperature and/or flow rate of coolant fluid may be adjusted to provide adequate cooling and/or other temperature control of the ultrasound transmission member 30.

In addition to infusing coolant fluid into and/or through the catheter device 10, the injection pump 69 may alternatively be utilized to infuse irrigation fluid into the lumen 18 of the catheter body 12 for purposes of removing debris from within the lumen of a vessel and/or forming a fluidic column to remove blood from the region of the distal head 34.

In addition, the injection pump 69 may be utilized to infuse a radiographic contrast medium into the catheter device 10 for purposes of imaging. Examples of iodinated radiographic contrast media which may be selectively infused into the catheter device 10 via the injection pump 69 are commercially available as Angiovist 370 from Berlex Labs, Wayne, N. J. and Hexabrix from Malinkrodt, St. Louis, Mo.

Moreover, drugs such as TPA, urokinase and streptokinase can be delivered via the infusion port or sidearm 73, through the lumen 18 and through the fluid outflow channel 48 to the region of the vessel that is being treated. The delivery of such drugs can cause the surrounding vessel to undergo smooth muscle relaxation due to the application of ultrasonic energy and the improved drug absorption by the tissue and cells.

Referring back to FIGS. 2 and 3, a guidewire 50 can be extended through the lumen 18 of the catheter body 12 and through a central bore 52 provided in the distal head 34. The central bore 52 has a generally straight proximal section 54 with a proximal opening 55 that opens into the lumen 18. The proximal section 54 communicates with a flared distal section 56 that opens into a distal opening 58 having a larger diameter than the diameter of the central bore 52 along the proximal section 54 and the proximal opening 55. Alternatively, the proximal section 54 can be provided with a very short length so that it effectively defines a proximal opening 55 for the flared distal section 56. The fluid outflow channel 48 is offset from the center of the distal head 34 and the central bore 52.

The guidewire 50 has a constant-diameter proximal section 62 connected at its distal end to a tapered section 64. The diameter of the tapered section 64 decreases distally from the diameter of the proximal section 62 to a smaller diameter intermediate section 67 at its distal end. The intermediate section 67 has a constant diameter that is smaller than the diameter of the proximal section 62, and has a ball 68 centered at its distal end. A distal section 70 is connected to the distal side of the ball 68. The length of the distal section 70 is preferably longer than the length of the occlusion to be crossed. The distal section 70 includes a core wire surrounded by a radiopaque coil 72 which is brazed or otherwise connected to the core wire of the distal section 70 at its opposing ends, to form a non-traumatic tip 74 for the guidewire 50. The ball 68 preferably has a diameter that is larger than the intermediate section 67 of the guidewire, and larger than the central bore 52 at the proximal region 54. By reducing the diameter of the guidewire 50 towards its distal end, the flexibility of the guidewire 50 is improved. Although the guidewire 50 is illustrated as having a reduced diameter tapered section 64 and intermediate section 67, it is possible to provide the guidewire 50 with the same diameter throughout its length.

The core guidewire 50 is preferably made of a material that is strong and provides torquability. Such a material can include, but is not limited to, SST or a superelastic material, or a nickel titanium alloy such as that which was described above in connection with the ultrasound transmission member 30. The ball 68 is made from a hard, lubricious precision material, such as stainless steel, synthetic ruby or sapphire. The coil 72 can be made, for example, from SST or platinum, and is preferably made radiopaque by providing radiopaque markers or by forming the coil together with a quantity of radiodense fillers, using methods and materials similar to those described above in connection with the distal head 34.

The ball 68 of the guidewire 50 is adapted to be engaged and secured inside the central bore 52 of the distal head 34 to create a narrowed distal extension of the catheter body 12. In this regard, the ball 68 also operates to transfer ultrasound vibrations from the distal head 34 to the distal section 70 of the guidewire 50, as explained in greater detail below. The diameter of the distal opening 58 of the central bore 52 is preferably larger than the diameter of the ball 68, but the diameter of the proximal-most part of the flared distal section 56 is preferably smaller than the diameter of the ball 68 so that the ball 68 is retained inside the flared distal section 56 and cannot pass into the central bore 52 at the proximal section 54, as shown in FIG. 3. Therefore, the ball 68 can be advanced distally of the distal head 34 (see FIG. 2), and can also be retracted proximally until it is secured inside the flared distal section 56 of the central bore 52 (see FIG. 3). Similarly, when the ball 68 is disengaged from the central bore 52, the guidewire 50 and the catheter 10 can be moved axially with respect to each other so that the guidewire 50 can act as a conventional guidewire.

Although a ball 68 has been illustrated in the embodiment of FIGS. 2 and 3 as providing the mechanical engagement between the guidewire 50 and the distal head 34, it is also possible to provide the guidewire 50 with other enlarged configurations that can be adapted to engage the distal head 34. Such enlarged configurations can take the form of bumps or ridges that are provided at the distal end of the intermediate section 67. The engagement of the ball 68 inside the flared distal section 56 can be accomplished, for example, by a friction interference fit.

The catheter device 10 in FIG. 1 is illustrated as a "monorail" catheter device, in which the guidewire 50 extends along the lumen 18 of the catheter body 12 adjacent the distal end 16 and exits the catheter body 12 through an exit port 86 adjacent but slightly proximal from the distal end 16. However, it is also possible to provide the catheter device 10 as an "over-the-wire" catheter device without departing from the spirit and scope of the present invention. In an "over-the-wire" catheter device, the guidewire 50 would extend along the entire lumen 18 of the catheter body 12 and exit at the proximal connector 21. The structural and operative principles of "monorail" and "over-the-wire" guidewire techniques are well known to those skilled in the art, and are not further discussed herein.

Figure 4:
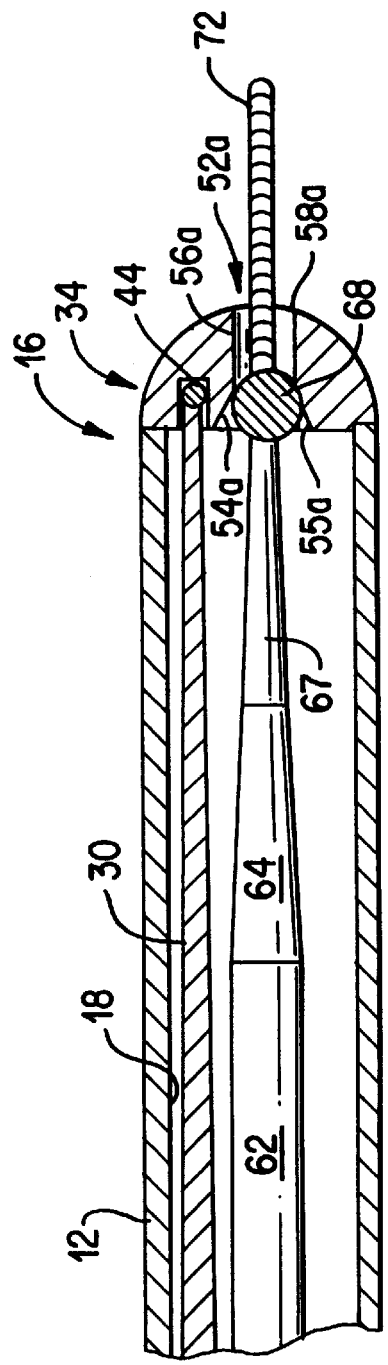
FIG. 4 is a cross-sectional view of the distal end of a second embodiment of an ultrasound catheter and guidewire that can be used with the system of FIG. 1.

As an alternative, as illustrated in FIG. 4, the central bore 52 can be modified so that the modified bore 52 has a flared proximal section 54a having a proximal opening 55a that opens into the lumen 18, and a generally straight distal section 56a that opens at a distal opening 58a that is smaller than the proximal opening 55a. The remainder of the catheter 12, the ultrasound transmission member 30 and the guidewire 50 may be the same as those illustrated in FIGS. 2 and 3 above. In this embodiment, the diameter of the proximal opening 55a of the central bore 52a is preferably larger than the diameter of the ball 68, but the diameter of the distal-most part of the flared proximal section 54a is preferably smaller than the diameter of the ball 68 so that the ball 68 is retained inside the flared proximal section 54a and cannot pass into the central bore 52a at the distal section 56a, as shown in FIG. 4. Alternatively, the distal section 56a can be provided with a very short length so that it effectively defines a distal opening 58a for the flared proximal section 54a. Therefore, the ball 68 can be retracted proximally into the lumen 18, but cannot extend outside the distal head 34 into the blood vessel. Similarly, when the ball 68 is disengaged from the central bore 52a, the guidewire 50 and the catheter 10 can be moved axially with respect to each other so that the guidewire 50 can act as a traditional guidewire. In this regard, the guidewire 50 can also be retracted to be exchanged according to conventional guidewire techniques that are well-known to those skilled in the art.

Figure 5:
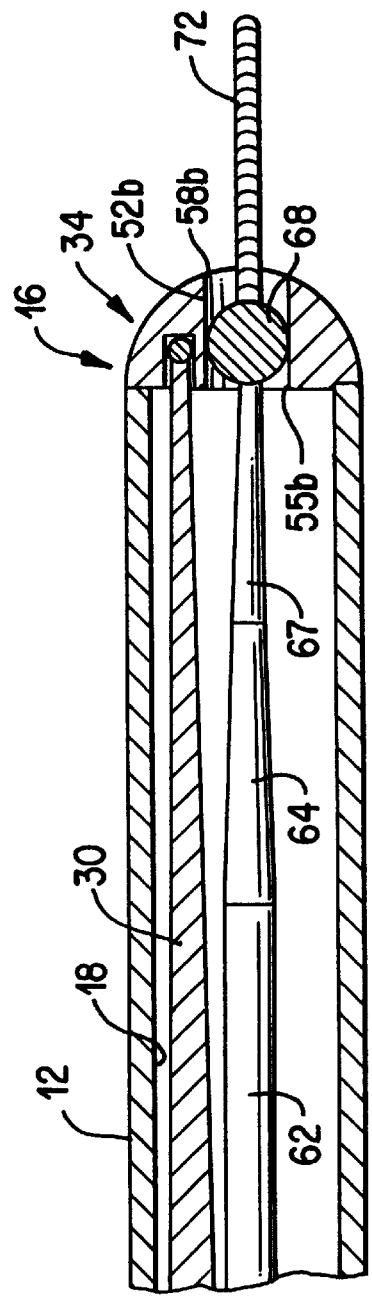
FIG. 5 is a cross-sectional view of the distal end of a third embodiment of an ultrasound catheter and guidewire that can be used with the system of FIG. 1.

As a further alternative, as illustrated in FIG. 5, the central bore 52 can be modified so that it has generally the same diameter throughout, with the diameter of the modified central bore 52b slightly smaller than the diameter of the ball 68 to allow the ball 68 to be secured therein by friction interference fit. The proximal opening 55b and the distal opening 58b preferably have the same diameter as the bore 52b. In this embodiment, the ball 68 may be advanced distally from the distal head 34, or proximally retracted into the lumen 18 of the catheter body 12 so that the guidewire 50 can be moveable back and forth within the catheter body 12.

Figure 6:
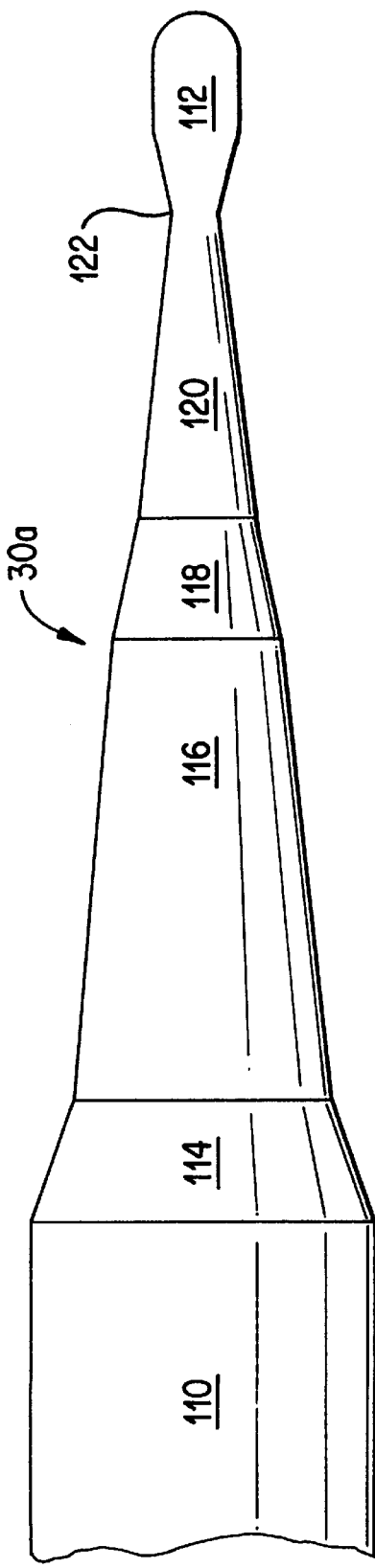
FIG. 6 is a partial cross-sectional view of the distal end of an ultrasound transmission wire that can be used with the system of FIG. 1.
Figure 7:
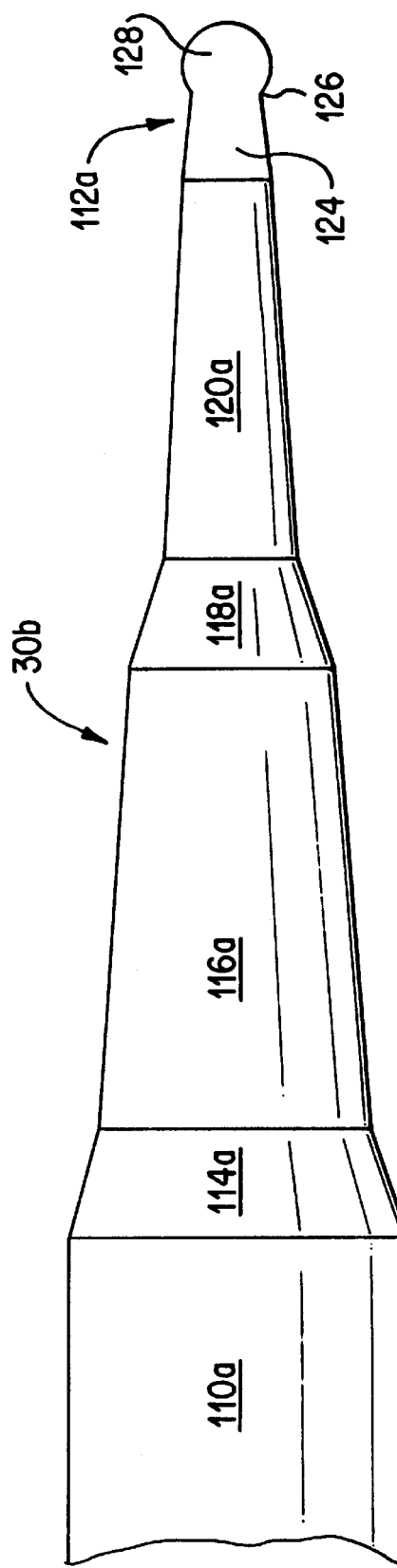
FIG. 7 is a partial cross-sectional view of the distal end of another ultrasound transmission wire that can be used with the system of FIG. 1.

FIGS. 6 and 7 illustrate two alternative embodiments of the ultrasound transmission member 30 according to the present invention that can be used with the catheter 12. Referring to FIG. 6, the transmission member 30a has a proximal section 110 having a constant outer diameter, an enlarged distal end 112, and a plurality of progressively tapered sections 114, 116, 118 and 120 extending from the proximal section 110 to the distal end 112. The tapered sections nearer the proximal section 110 have a greater profile or dimension than the tapered sections nearer the distal end 112. The enlarged distal end 112 has an ovoid configuration and is adapted to be received into, and is welded, bonded or attached to, the bore 40 of the distal head 34. The distal end 112 has a greater profile or dimension than the distal-most extent 122 of the tapered section 120 to tolerate stress associated with the attachment of the distal end 112 to the distal head 34. The lengths of each tapered section 114, 116, 118, 120 can range from 0.5 cm to 30 cm, and each tapered section can have the same or different lengths. The progressively tapered sections 114, 116, 118, 120 improve ultrasound propagation through the transmission member 30a by providing higher amplitude and a smoother transition between the respective sections 114, 116, 118, 120.

The ultrasound transmission member 30b of FIG. 7 has the same configuration as the ultrasound transmission member 30a of FIG. 6, except that the distal end 112a has a proximal tapered neck 124 that decreases in cross-sectional diameter from its proximal end to its distal end to a distal-most extent 126 that has the smallest cross-sectional diameter along the entire ultrasound transmission member 30b. At the distal-most extent 126, the distal end 112a transitions into an enlarged spherical ball 128 that is adapted to be received into, and is welded, bonded or attached to, the bore 40 of the distal head 34.

The combined catheter device 10 and guidewire 50 of the present invention is effective in crossing completely occluded obstructions in a blood vessel, and in removing obstructive material therefrom after the obstruction has been crossed. In use, the guidewire 50 can be percutaneously introduced and advanced along the patient's vasculature until its distal tip 74 is adjacent obstructive material OB which completely occludes this blood vessel BV. The catheter device 10 is then advanced along the guidewire 50 until the distal end 16 of the catheter device 10 is adjacent the obstruction OB. At this point, by gripping and manipulating the proximal ends of the catheter device 10 and the guidewire 50, the guidewire 50 can be "docked" in the distal head 34 of the catheter device 10 by causing the ball 68 to be secured inside the central bore 52 in the manner described above. Alternatively, the guidewire 50 is first "docked" in the distal head 34, and the catheter device 10 and guidewire 50 can be percutaneously introduced and advanced together along the patient's vasculature. When the guidewire 50 has been secured at the distal head 34 of the catheter device 10, the guidewire 50 in effect becomes a distal extension of the catheter device 10. As a result, when ultrasound energy is applied to the distal head 34 via the ultrasound transmission member 30, the ultrasound energy is transferred onto the distal section 70 of the guidewire 50 via the ball 68, so that the distal section 70 and its tip 74 will vibrate. The narrowed profile of the distal tip 74 of the guidewire 50 allows the distal section 70 of the guidewire 50 to search for the softer portions of the obstruction OB that can be broken down. By simultaneously torquing the guidewire 50 while ultrasound energy is being applied to the distal section 70 of the guidewire 50 via the distal head 34, the distal section 70 of the guidewire 50 becomes a pathfinding probe which can create a channel 80 through the obstruction OB. This is illustrated in FIGS. 8A and 8B. At this time, the distal section 70 extends through the channel 80 and the distal tip 74 is on the other side of the obstruction OB.

Figure 8C:
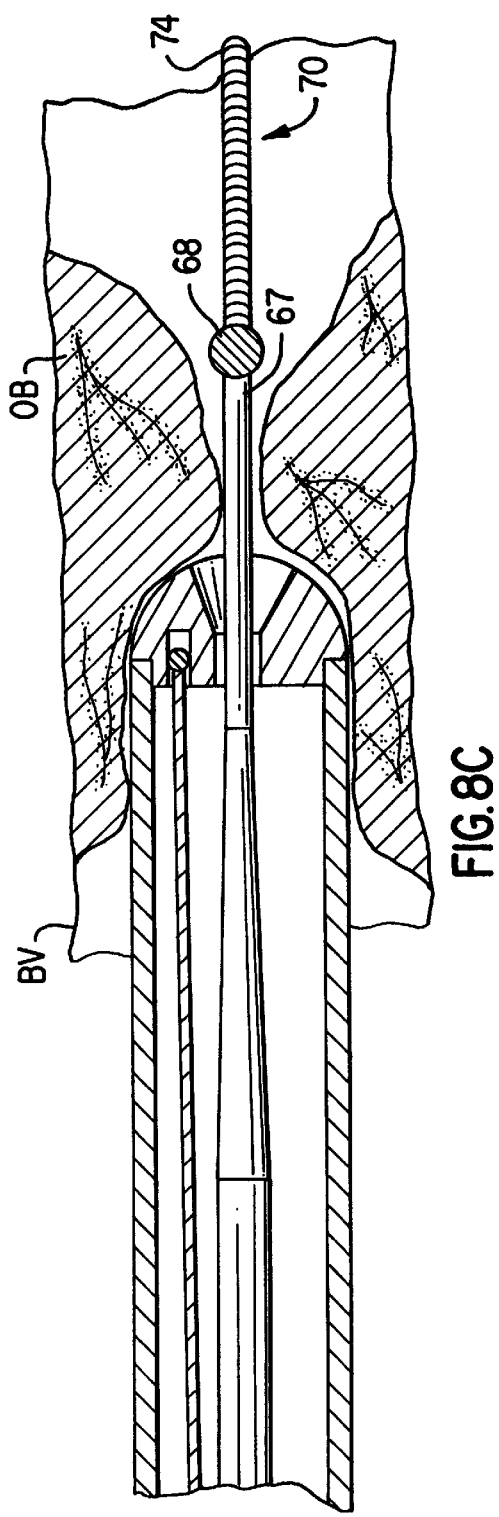

After the channel 80 has been created, the ultrasound signal generator 24 is turned off and the guidewire 50 can be disengaged from the distal head 34 by gripping and manipulating the proximal ends of the catheter device 10 and the guidewire 50. The guidewire 50 can be advanced through the channel 80 separately from the catheter device 10 so that the ball 68 also extends through the channel 80 and is disposed on the other side of the obstruction OB. The guidewire 50 can be advanced even further for support to increase safety. The distal head 34 can now be advanced along the guidewire 50 and against the obstructive material OB, and application of ultrasound energy to the distal head 34 will cause obstructive material OB to be removed, as shown in FIG. 8C. Since the guidewire 50 has been disengaged from the distal head 34 of the catheter device 10, no ultrasound energy is transferred through the guidewire 50 and all the ultrasound energy will be concentrated on the distal head 34. After all desired obstructive material OB has been removed, the catheter device 10 may be withdrawn and removed. Adjunct balloon angioplasty or stenting can be performed if desired.

If the distal head 34 of the catheter device 10 employs the central bore 52a of FIG. 4, the guidewire 50 must be "docked" in the distal head 34, and the catheter device 10 and the guidewire 50 percutaneously introduced and advanced together along the patient's vasculature. After the guidewire 50 has created a channel 80 through the obstructive material OB, the ball 68 is disengaged from the distal head 34 and the guidewire 50 is retracted proximally. However, the length of the distal section 70 of the guidewire 50 is preferably long enough so that its distal tip 74 will still extend distally of the obstructive material OB. As a result, the distal head 34 can now be advanced along the distal section 70 of the guidewire 50 and against the obstructive material OB, and application of ultrasound energy to the distal head 34 will cause obstructive material OB to be removed.

If the distal head 34 of the catheter device 10 employs the central bore 52b of FIG. 5, either method described above can be employed. In other words, after the ball 68 has been disengaged from the distal head 34, the guidewire 50 may be advanced distally or retracted proximally to facilitate advancement of the distal head 34 along the guidewire 50 and against the obstructive material OB.

Figure 9:
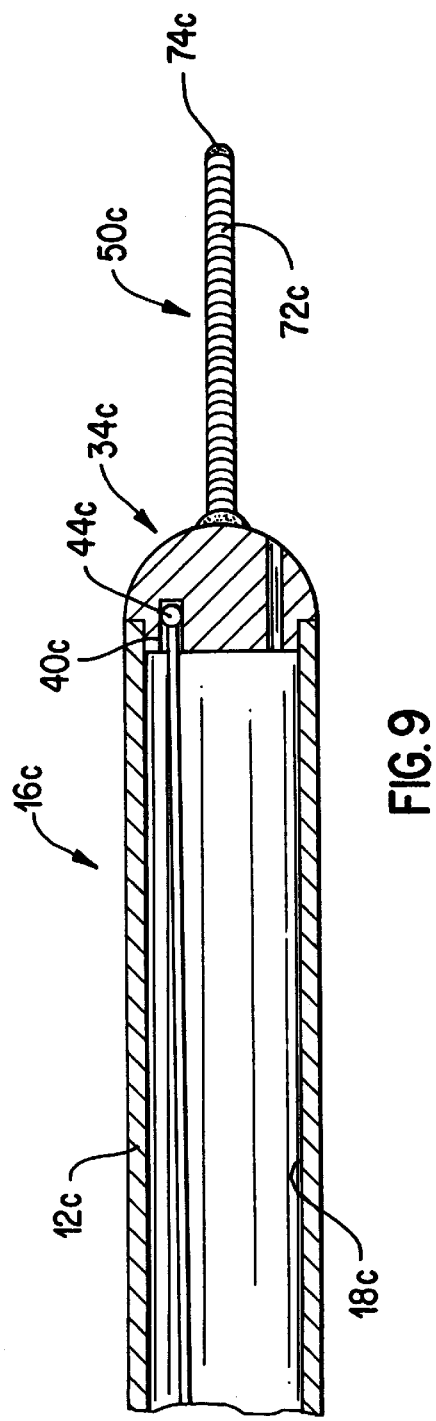
FIG. 9 is a cross-sectional view of the distal end of a fourth embodiment of an ultrasound catheter and guidewire that can be used with the system of FIG. 1.

FIG. 9 illustrates a "fixed-wire" approach to the present invention, as contrasted with the "monorail"/"over-the-wire" approaches described hereinabove. The distal end 16c of the catheter body 12c is similar to the distal end 16 of catheter body 12, in that it is provided with a single lumen 18c terminating in a distal head 34c, with an ultrasound transmission member 30c extending therethrough. The transmission member 30c has a distal ball 44c secured inside a bore 40c in the distal head 34c. A fluid outflow channel 48c also extends longitudinally through the distal head 34c in a manner offset from the center of the distal head 34c.

The distal end 16c differs from the distal end 16 in that it is provided with a fixed guidewire 50c attached to and extending distally from the center of the rounded distal head 34c. The length of the guidewire 50c is preferably longer than the length of the occlusion to be crossed. The guidewire 50c can be attached to the outer surface of the distal head 34c by welding, soldering, bonding, and other conventional attachment methods. The guidewire 50c preferably takes the form of the distal section 70 described above, in that it has a core wire surrounded by a radiopaque coil 72c.

When in use, the distal end 16c and its fixed guidewire 50c can be advanced along the patient's vasculature until its distal tip 74c is adjacent obstructive material OB which completely occludes this blood vessel BV. Since the guidewire 50c is in effect a distal extension of the distal end 16c, ultrasound energy that is applied to the distal head 34c via the ultrasound transmission member 30c will be transferred onto the guidewire 50c to cause the guidewire 50c to vibrate. By simultaneously torquing the guidewire 50c while ultrasound energy is being applied thereto, the guidewire 50c becomes a pathfinding probe which can create the channel 80 through the obstruction OB. After the channel 80 has been created, the distal head 34c will be adjacent the obstructive material OB, and application of ultrasound energy to the distal head 34c will cause obstructive material OB to be removed. In this embodiment, the guidewire 50c will be vibrated together with the distal head 34c to remove obstructive material OB. After all desired obstructive material OB has been removed, the catheter device 10 may be withdrawn and removed. Adjunct balloon angioplasty or stenting can be performed if desired.

Thus, the ultrasound catheter system according to present invention is capable of delivering ultrasound energy to create a channel to allow a guidewire to cross a completely occluded blood vessel. The ultrasound catheter system according to present invention can then be used to deliver ultrasound energy to remove obstructive material from the occlusion. As a result, the ultrasound catheter system according to present invention provides a combined and simplified ultrasound catheter system that is easy to use and is effective for both crossing a completely occluded blood vessel and removing obstructive material.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An ultrasound catheter system comprising:
   an elongate flexible catheter body having a proximal end, a distal end and at least one lumen extending longitudinally therethrough;
   an ultrasound transmission member extending longitudinally through the lumen of the catheter body, the ultrasound transmission member having a distal end, and a proximal end connectable to a separate ultrasound generating device;
   a distal head positioned on the distal end of the ultrasound transmission member and having a bore extending therethrough said bore having a flared opening; and
   a guidewire extending through the bore and having a portion that frictionally engages the flared opening of the bore to create a coupling so that ultrasound energy transmitted from the ultrasound transmission member will be transferred from the distal head directly to the guidewire.

2. The system of claim 1, wherein the bore also has a proximal opening, the distal opening having a larger diameter than the proximal opening, and wherein the portion has an enlarged member that engages the distal opening of the bore to couple the guidewire to the distal head.

3. The system of claim 1, flared opening is proximal opening and the wherein the bore also has with a distal opening, the proximal opening having a larger diameter than the distal opening, and wherein the portion has an enlarged member that engages the proximal opening of the bore to couple the guidewire to the distal head.

4. The system of claim 1, wherein the ultrasound transmission member is made from a material that includes nickel having an atomic weight ranging from 50.50 to 51.50.

5. The system of claim 1, wherein the guidewire has a constant-diameter proximal section, and a tapered section extending distally from the proximal section and having a distal end, the guidewire further including an enlarged member provided at the distal end of the tapered section, and a distal section extending distally from the enlarged member, wherein the enlarged member has a diameter that is greater than the dimension of the distal end of the tapered section.

6. The system of claim 1, wherein the ultrasound transmission member has a proximal region adjacent the proximal end, an enlarged distal end, and an intermediate region between the proximal region and the distal end of the ultrasound transmission member, wherein the intermediate region has a distal end and a dimension which is smaller than the dimension of the proximal region, and wherein the enlarged distal end of the ultrasound transmission member has a dimension which is larger than the dimension of the distal end of the intermediate region.

7. The system of claim 1, wherein the ultrasound transmission member has a proximal section and a spherical distal tip having a diameter which is preferably larger than the outer diameter of the transmission member along the proximal section.

8. A method of crossing an occlusion inside a blood vessel, comprising the steps of:
   a. providing a system having:
      an elongate flexible catheter body having a proximal end, a distal end and at least one lumen extending longitudinally therethrough;
      an ultrasound transmission member extending longitudinally through the lumen of the catheter body, the ultrasound transmission member having a distal end, and a proximal end connectable to a separate ultrasound generating device; and a distal head positioned on the distal end of the ultrasound transmission member;

b. delivering a guidewire inside the blood vessel to the site of the occlusion, the guidewire having a distal end;

c. passing the system over the guidewire without coupling the system to the guidewire;

d. coupling the guidewire to the distal head; and e. causing the distal end of the guidewire to create a channel in the occlusion to thereby cross the occlusion.

9. The method of claim 8, wherein step (e) further includes the step of:

delivering ultrasound energy to the distal section of the guidewire via the distal head.

10. The method of claim 9, wherein step (d) further includes the step of:

frictionally engaging the guidewire with the distal head.

11. The method of claim 8, further including the steps of:

disengaging the coupling of the guidewire and the distal head;

advancing the guidewire distally of the occlusion;

advancing the distal head along the guidewire and against the occlusion; and delivering ultrasound energy to the distal head.

12. The method of claim 8, further including the steps of:

disengaging the coupling of the guidewire and the distal head;

retracting the guidewire proximally of the occlusion;

advancing the distal head along the guidewire and against the occlusion; and delivering ultrasound energy to the distal head.

13. The method of claim 8, wherein step (d) further includes the step of:

providing an enlarged member along the length of the guidewire;

providing the distal head with a longitudinal bore; and frictionally engaging the enlarged member with the longitudinal bore.

* * * * *